United States Patent [19]
Yukio et al.

[11] 3,962,345
[45] June 8, 1976

[54] ALKYL PHENYL ETHER DERIVATIVES

[75] Inventors: Aoki Yukio; Takeuchi Susumu, both of Omiya; Wakita Shizuo; Kato Shoichi, both of Ageo; Ishida Shuichi, Omiya, all of Japan

[73] Assignee: Nippon Kayaku Co., Ltd., Tokyo, Japan

[22] Filed: June 25, 1974

[21] Appl. No.: 482,861

[30] Foreign Application Priority Data
July 19, 1973 Japan................................. 48-82272

[52] U.S. Cl.......................... 260/607 R; 260/609 F; 424/337; 260/607 A
[51] Int. Cl.².............. C07C 147/06; C07C 149/32
[58] Field of Search ..................... 260/609 F, 607 A; 424/337

[56] References Cited
UNITED STATES PATENTS
3,804,904    4/1974    Bentley et al. ................... 260/609 F FOREIGN PATENTS OR APPLICATIONS
1,288,450    9/1972    France............................. 260/609 F
2,116,579   12/1971    France............................. 260/607 A OTHER PUBLICATIONS
Chem. Abst., vol. 57, pp. 4202–4203, (1962).

Primary Examiner—Elbert L. Roberts
Assistant Examiner—D. R. Phillips
Attorney, Agent, or Firm—Russell & Nields

[57] ABSTRACT

The present invention relates to alkyl phenyl ether derivatives of the formula (I)

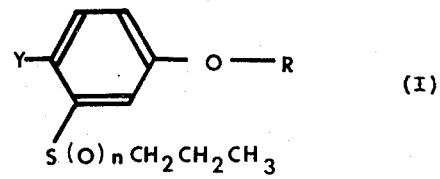

(wherein Y represents methyl radical or chlorine atom, R represents an alkyl having from 1 to 8 carbon atoms, $n$ is an integer of 0, 1 of 2); said compounds are manufactured by condensing, if necessary in the presence of an alkaline compound, a compound expressed by the formula (II)

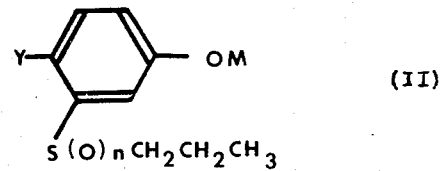

(wherein Y and $n$ have the same meanings as defined hereinbefore, M represents hydrogen atom or an alkali metal atom.) with a compound expressed by the formula (III)

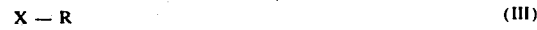

X — R                                    (III)

(wherein X represents a halogen atom and R has the same meaning as defined hereinbefore). Said new compounds have an acaricidal effect, therefore, the compounds are used as acaricide.

1 Claim, No Drawings

ALKYL PHENYL ETHER DERIVATIVES

BACKGROUND OF THE INVENTION

It is well known that leaf mites, for example, carmine mite or *Tetranychus telarius*, two-spotted spider mite or *Tetranychus ulticae*, citrus red mite or *Panonychus citri*, European red mite or *Panonychus ulmi*, sweet cherry spider mite or *Tetranychus viennensis*, Kanzawa spider mite or *Tetranychus kanzawai* and Clover mite or *Bryobia praetiose* koch give serious damage to plants, and particularly, two-spotted spider mite (*Tetranychus ulticae*) inflicts great and heavy damage on agriculturally important fruits such as apples, pears, peaches, etc., vegetables such as egg-plants, cucumbers, etc., various kinds of beans, hops, mulberry, carnation, etc., and citrus red mite (*Panonychus citri*) also gives serious damage to citrus fruits, pears, apples, peaches, mulberries, etc., which are important from the viewpoint of fruit-culture. In order to remove or prevent the mite infliction on the crops or fruits, many acaricides have been used. However, the fact is that the mites disadvantageously tend to have resistance to most of the known acaricides, which leads to reduction in the acaricidal effect thereof.

Therefore, it is strongly desired to develop a novel acaricide for overcoming this disadvantage.

SUMMARY OF THE INVENTION

We have conducted an extensive study seeking a novel acaricide and discovered that the compounds expressed by the above-mentioned formula (I) have particular and excellent effects in the prevention of leaf mites such as carmine mite (*Tetranychus telarius*), two-spotted spider mite (*Tetranychus ulticae*) citrus red mite (*Panonychus citri*), and European red mite (*Panonychus ulmi*).

The compounds of the formula (I) are characterized by low toxicity to warm-blooded animals, and also characterized by no damage to the plants or vegetables mentioned above.

The compounds expressed by the formula (I) are prepared by condensing a compound of formula (II) with a compound of formula (III), if necessary, in the presence of an alkaline compound. In this reaction, the compound of formula (II) is usually used in an amount of 0.8 to 1.5 moles per mole of the compound of formula (III). However, the compound of formula (II) can be used in a larger amount, also serving as a solvent without use of an inactive solvent. When M of formula (II) is hydrogen, the reaction is conducted in the presence of an alkaline compound such as alkali hydroxide, for example, potassium hydroxide and sodium hydroxide and alkaline carbonate, for example, potassium carbonate.

These alkaline compounds are usually used slightly in excess of an amount which is required in the chemical equivalent.

The reaction of compounds of formulae (II) and (III) can be smoothly conducted by the use of a solvent, for example, alchols, aceton, benzene and an aprotic polar solvent such as dimethylsulfoxide, dimethylformamide, dimethylacetamide, or diethylglycol diethyl ether, but the use of these solvents is not essentially required.

The reaction temperature may be varied depending on the kinds of compounds and solvent used, but is within a range of 0° to 160°C, preferably 20° to 100°C.

If a compound of formula (I) with $n=0$ is oxidized by the use of an oxidizing agent, the compound obtained hs $n=1$ or $n=2$.

The oxidizing agent used in the oxidation are, for example, hydroperoxide, fuming nitric acid, permanganate such as potassium permanganate and persulfate such as potassium persulfate.

The compounds of formula (II) used in the preparation of the compounds of formula (I) are, for example, 3-propylthio-4-methylphenol, 3-propylsulfinyl-4-methylphenol, 3-propylsulfonyl-4-methylphenol, 3-propylthio-4-chlorophenol, 3-propylsulfinyl-4-chlorophenol, 3-propylsulfonyl-4-chlorophenol, sodium salt and potassium salt thereof.

The compounds of formula (III) used in the preparation the compounds of formula (I) are, for example, methyl chloride, methyl bromide, methyl iodide, ethyl chloride, ethyl bromide, propyl chloride, propyl iodide, propyl bromide, n-butyl chloride, i-butyl chloride, n-butyl bromide, n-butyl iodide, n-amyl chloride, n-amyl bromide, n-amyl iodide, n-hexyl chloride, n-hexyl bromide, n-hexyl iodide, n-heptyl chloride, n-heptyl bromide, n-heptyl iodide, n-octyl chloride and n-octyl bromide.

The representative compounds of formula (I) are shown in the following Table 1.

Table 1

| Compound Number | Y | R | n | Boiling point, melting point or refractive index |
|---|---|---|---|---|
| 1 | CH$_3$ | CH$_3$ | 0 | bp 114–115.2 °C/2mmHg |
| 2 | CH$_3$ | CH$_3$ | 2 | bp 174–176 °C/1.5mmHg |
| 3 | CH$_3$ | C$_3$H$_7$(n) | 0 | $n_D^{25}$ = 1.5383 |
| 4 | CH$_3$ | C$_3$H$_7$(n) | 1 | mp 52–53 °C |
| 5 | CH$_3$ | C$_4$H$_9$(n) | 0 | bp 126–127 °C/2mmHg |
| 6 | CH$_3$ | C$_4$H$_9$(n) | 1 | mp 54–54.5 °C |
| 7 | CH$_3$ | C$_4$H$_9$(n) | 2 | $n_D^{25}$ = 1.5208 |
| 8 | CH$_3$ | C$_5$H$_{11}$(n) | 0 | bp 136–139 °C/2mmHg |
| 9 | CH$_3$ | C$_5$H$_{11}$(n) | 1 | $n_D^{25}$ = 1.5286 |
| 10 | CH$_3$ | C$_5$H$_{11}$(n) | 2 | $n_D^{25}$ = 1.5170 |
| 11 | CH$_3$ | C$_6$H$_{13}$(n) | 0 | bp 142–146 °C/2mmHg |
| 12 | CH$_3$ | C$_6$H$_{13}$(n) | 1 | $n_D^{25}$ = 1.5248 |
| 13 | CH$_3$ | C$_6$H$_{13}$(n) | 2 | $n_D^{25}$ = 1.5142 |
| 14 | CH$_3$ | C$_7$H$_{15}$(n) | 0 | bp 159–162 °C/2mmHg |
| 15 | CH$_3$ | C$_7$H$_{15}$(n) | 1 | $n_D^{25}$ = 1.5215 |
| 16 | CH$_3$ | C$_7$H$_{15}$(n) | 2 | $n_D^{25}$ = 1.5108 |
| 17 | Cl | C$_2$H$_5$ | o | mp 58–59 °C |
| 18 | Cl | C$_2$H$_5$ | 1 | $n_D^{25}$ = 1.5462 |
| 19 | Cl | C$_3$H$_{11}$(n) | 0 | $n_D^{25}$ = 1.5421 |
| 20 | Cl | C$_5$H$_{11}$(n) | 1 | $n_D^{25}$ = 1.5328 |
| 21 | Cl | C$_5$H$_{11}$(n) | 2 | $n_D^{25}$ = 1.5256 |
| 22 | Cl | C$_6$H$_{13}$(n) | 0 | $n_D^{25}$ = 1.5380 |
| 23 | Cl | C$_6$H$_{13}$(n) | 1 | $n_D^{25}$ = 1.5330 |
| 24 | Cl | C$_6$H$_{13}$(n) | 2 | mp 60–61 °C |

The method for the preparation of the compound of formula (I) will be illustrated in more details by the following synthesizing example.

SYNTHESIZING EXAMPLE 1 n-Amyl-(4-methyl-3-propylthio) phenyl ether 12g (0.066 mole) of 4-methyl-3-propylthiophenol (bp 136°–138°C/3mmHg, $n_D^{25}$ 1.5762), 3.6g (0.066 mole) of potassium hydroxide and 30 ml of dimethylformamide were mixed and the mixture was heated to a temperature above 90°C to obtain a complete solution thereof. Then, the resultant solution was cooled down to room temperature and, while further cooling the solution in an ice bath, 9.5g (0.063 mole) of n-amyl bromide was added thereto. After the addition of amyl bromide, the ice bath was removed and then the solution was stirred for 5 hours at room temperature. After completion of reaction, the reaction mixture was poured into 200 ml of water. A brown oily layer formed on an aqueous layer was extracted with benzene. The extract was washed successively with 5% (by weight) hydrochloric acid solution, 5% (by weight) sodium hydroxide solution and water. After the extract thus washed was dried by sodium sulfate, benzene was removed by distillation to obtain 16.6 g (99.6% of theoretical) of n-amyl-(4-methyl-3-propylthio)phenyl ether. After purification by distillation, colorless and transparent oil having a boiling point of 136°C–139°C was obtained.

Elemental Analysis (as $C_{15}H_{24}OS$): Found: C: 71.19%, H: 9.50%. Calculated: C: 71.38%, H: 9.58%.

SYNTHESIZING EXAMPLE 2 n-Amyl-(4-methyl-3-propylsulfinyl) phenyl ether 4.5 g (0.0178 moles) of n-amyl-(4-methyl-3-propylthio)phenyl ether which was obtained by Synthesizing Example 1 was dissolved in 30 ml of acetic acid.

The solution was cooled below 10°C. After 3.0 g (0.0267 mole) of 30% (by weight) hydroperoxide solution was added to the solution, the resultant solution was stirred for 2 hours at room temperature.

The resultant reaction mixture was poured into 100 ml of water and then benzene was added to the aqueous reaction mixture to extract the reaction product. The extract was washed successively with 5% (by weight) sodium carbonate solution and water, and dried with sodium sulfate. After benzene was removed by distillation, 4.5 g (94.2% of theoretical) of n-amyl-(4-methyl-3-propyl-sulfynyl) phenyl ether was obtained. The compound, after purification by distillation, was colorless and transparent oil having refractive index of $n_D^{25}$ 1.5286.

Elemental Analysis (as $C_{15}H_{24}O_2S$): Found: C: 67.01%, H: 8.98%. Calculated: C: 67.12%, H: 9.01%.

SYNTHESIZING EXAMPLE 3 n-Amyl-(4-methyl-3-propylsulfonyl) phenyl ether 4.5 g (0.0178 mole) of n-amyl-(4-methyl-3-propylthio) phenyl ether was dissolved in 30 ml of acetic acid.

After the solution was cooled below 10°C, 4.0 g of 30% (by weight) hydroperoxide solution was added into the solution. The mixture was reacted for 2 hours at 90°C.

The reactant was treated by the same procedure as Synthesizing Example 2 and n-amyl-(4-methyl-3-propylsulfonyl) phenyl ether, which was colorless and transparent oil having refractive index of $n_D^{25}$ 1.5170, was obtained.

Elemental Analysis as $C_{15}H_{24}O_3S$: Found: C: 63.30%, H: 8.30%. Calculated: C: 63.35%, H: 8.51%.

SYNTHESIZING EXAMPLE 4 n-Amyl-(4-chloro-3-propylsulfinyl) phenyl ether 2 g (0.009 mole) of 4-chloro-3-propylsulfinyl phenol (mp 80°–81°C), 1.3 g (0.009 mole) of potassium carbonate, 20 ml of dimethylacetamide and 1.4 g (0.009 mole) of n-amyl bromide were mixed and the resultant mixture was reacted at a temperature of 90°–100°C for 5 hours. After completion of the reaction, the reaction mixture was poured into water. Thereafter, the reaction product was extruded with benzene and the extract was washed with 5% sodium hydroxide solution and water, and dried with sodium sulfate. Then, benzene was removed by distillation and n-amyl-(4-chloro-3-propylsulfinyl) phenyl ether, which was colorless and transparent oil having refractive index of $n_D^{25}$ 1.5328, was obtained.

Elemental Analysis (as $C_{14}H_{21}ClO_2S$). Found: C: 58.21%, H: 7.30%. Calculated: C: 58.22%, H: 7.33%.

SYNTHESIZING EXAMPLE 5

Methyl-(4-methyl-3-propylthio) phenyl ether 18.2 g (0.1 mole) of 4-methyl-3-propylthiophenol, 5.7 g (0.1 mole) of potassium hydroxide and 50 ml of dimethylacetamide and 17.0 g (0.12 mole) of methyl iodide were mixed and the resultant mixture was reacted at the room temperature for 5 hours. After completion of reaction, the reaction mixture was poured into 200 ml of water. A brown oily layer formed on an aqueous layer was extracted with benzene. Extract was washed with 5% solution of sodium hydroxide and water, and dried with sodium sulfate. Then benzene was removed by distillation and 17.1 g (87.2% of theoretical) methyl-(4-methyl-3-propylthio)phenyl ether, which was colorless and transparent oil having a boiling point of 114°–115.2°C/2mmHg, was obtained.

Elemental Analysis (as $C_{11}H_{16}OS$): Found: C: 67.37%, H: 8.17%. Calculated: C: 67.35%, H: 8.16%.

SYNTHESIZING EXAMPLE 6

Propyl-(4-methyl-3-propylthio) phenyl ether 11.0 g (0.0603 mole) of 4-methyl-3-propylthiophenol, 3.4 g (0.0603 mole) of potassium hydroxide and 30 ml of dimethylacetamide and 7.5 g (0.058 mole) of propyl bromide were mixed and the resultant mixture was reacted at the room temperature for 5 hours. After completion of reaction, the reaction mixture was poured into 200 ml of water. A brown oily layer formed on an aqueous layer was extracted with benzene. Extract was washed with 5% sodium hydroxide solution and water, and dried with sodium sulfate. Then benzene was removed by distillation and 1.8 g (87% of theoretical) propyl-(4-methyl-3-propylthio) phenyl ether, which was colorless and transparent oil having refractive index of $n_D^{25}$ 1.5383, was obtained.

Elemental Analysis (as $C_{13}H_{20}OS$): Found: C: 69.69%, H: 8.96%. Calculated: C: 69.64%, H: 8.93%.

SYNTHESIZING EXAMPLE 7 n-Butyl-(4-methyl-3-propylsulfonyl) phenyl ether 11.8 g (0.055 mole) of 4-methyl-3-propylsulfonylphenol and 3.1 g (0.055 mole) of potassium hydroxide are dissolved completely in 50 ml of dimethylformamide with heating. 6.9 g (0.05 mole) of n-butyl bromide was added to the solution and reacted at 100°–110°C for 5 hours with heating.

After the reaction, the resulting mixture was cooled, added to 200 ml of water and extracted with benzene. The extract was washed with 5% sodium hydroxide solution and water, and dried with sodium sulfate. Then benzene was removed by distillation and 10.4 g (77% of theoretical) n-butyl-(4-methyl-3-propylsulfonyl) phenyl ether, which was colorless and transparent oil having refractive index of $n_D^{25}$ 1.5208, was obtained.

Elemental Analysis (as $C_{14}H_{22}O_3S$): Found: C: 62.34%, H: 8.12%. Calculated: C: 62.22%, H: 8.15%.

The compounds thus obtained have an excellent acaricidal activity, particularly the compounds represented by the formula (I) in which Y represents methyl radical or chlorine atom, R represents an alkyl having from 2 to 7 carbon atoms and $n$ is an integer of 0 or 1 have a very excellent acaricidal activity.

Accordingly, the compounds can be used as acaricide singly or in combination with one or more suitable adjuvants in the form of emulsion, wettable powder, powder or granule. The adjuvants include a carrier and a supplementary material which is usually employed in agricultural chemicals. The carrier mentioned herein is intended to mean a transferring material which is utilized for transferring active components to a place to which the components are applied. The carrier may be solid liquid or gaseous. That is to say, the solid carriers are, for example, clay, talc, bentonite, white carbon, kaolin, diatomaceous earth and silica. The liquid carriers are, for example, water, benzene, kerosene, alcohols, acetone, xylene, methylnaphthalene, cyclohexane, animal and plant oils, aliphatic acids and esters of aliphatic acid. And the gaseous carriers are air, nitrogen, carbon dioxide, freon and the like.

The supplementary material includes, for example, a spreader, an emulsifier, a sticking agent, a wetting or a surface active agent, namely polyoxyethylene alkylallyl ether, polyvinyl alchol, polyoxyethylene sorbitan monooleate, alkyldimethylbenzyl ammonium chloride, alkylbenzensulfonate, ligninsulfonate, an ester of higher alcohol of sulfuric acid, etc.

When the compound of the present invention is used for an acaricide in the form of an emulsion or a wettable powder, the concentration of the compound in the acaricide is within a range of 5–60 percent, preferably 10–40 percent by weight, and the acaricide is diluted with water within a range of 0.1–0.01 percent by weight before sprinkling, and the acaricide diluted is sprinkled in an amount of 100–1000 liter per 10 ares.

When used in the form of powder or granule, the concentration is within a range of 0.5–5 percent by weight and the acaricide is used within a range of 2–5 Kg per 10 ares.

The acaricides of the present invention are concretely illustrated by the following example.

COMPOSITION EXAMPLE 1 (EMULSION)

| | |
|---|---|
| n-Amyl-(4-methyl-3-propylthio) phenyl ether | 20 parts by weight |
| The mixture of xylene and methylnaphthalene | 65 parts by weight |
| The mixture of calcium alkylbenzene-sulfonate and the condensation products of alkylphenol and ethyleneoxide | 15 parts by weight |

The components mentioned above were mixed until a uniform solution was obtained. When used, the solution was diluted with water and the emulsion was obtained. The emulsion was sprinkled as acaricide.

COMPOSITION EXAMPLE 2 (WETTABLE POWDER)

| | |
|---|---|
| n-Amyl-(4-chloro-3-propylsulfinyl) phenyl ether | 20 parts by weight |
| Kaolin | 40 parts by weight |
| Clay | 25 parts by weight |
| Diatomaceous earth | 7.5 parts by weight |
| The mixture of sodium laurate and dinaphthylmethanesulfonic acid | 7.5 parts by weight |

The components mentioned above were mixed and pulverized into fine powder.

When used, the fine powder was diluted with water and the resultant mixture was sprinkled.

COMPOSITION EXAMPLE 3 (POWDER)

| | |
|---|---|
| n-Buthyl-(4-methyl-3-propylsulfinyl) phenyl ether | 3 parts by weight |
| Clay | 96 parts by weight |
| Synthetic hydrated silicic acid | 1 part by weight |

The components mentioned above were mixed and pulverized into powder. When used, the powder was scattered.

The acaricidal effect of the compounds of the present invention will be understood from the following experimental examples.

EXPERIMENTAL EXAMPLE 1

Female imagoes of two-spotted spider mites were inoculated on leaves of a kidney-bean. After 2 days of inoculation, the leaves were immersed for 10 seconds in a emulsion containing 0.04 percent by weight of a compound of the present invention. After 2 days of the treatment, the death and life of the mites were observed, and the living mites were removed from the leaves. The leaves were left as they were for 7 days and the number of unhatched eggs were examined. The results are shown in Table (II).

TABLE (II)

| | Mortality Rate of Two Spotted Spider Mite | |
|---|---|---|
| Compound No. | Mortality Rate | |
| | Imago % | Egg % |
| 1 | 76 | 68 |
| 3 | 100 | 94 |
| 4 | 100 | 100 |
| 5 | 100 | 97 |
| 6 | 100 | 100 |
| 8 | 100 | 100 |
| 9 | 100 | 100 |
| 10 | 89 | 82 |
| 11 | 100 | 100 |
| 12 | 100 | 100 |
| 13 | 89 | 78 |
| 14 | 100 | 100 |
| 15 | 100 | 100 |
| 17 | 100 | 100 |
| 18 | 78 | 92 |
| 19 | 100 | 100 |
| 20 | 100 | 100 |
| 21 | 94 | 88 |
| 22 | 100 | 100 |
| 23 | 100 | 100 |
| 24 | 94 | 82 |
| Non-treated | 2 | 0 |

When the wettable powder was used instead of emulsion in this example, about the same results were obtained.

EXPERIMENTAL EXAMPLE 2

A summer orange was cultivated in a porous pot having a diameter of 12 cm. All leaves except two were cut off. A birdlime was applied onto stalks of two leaves and ten female imagoes of citrus red mites were inoculated per leaf to allow them to deposit eggs for 2 days.

Then, solutions each containing 0.04 percent by weight of respective compounds in accordance with the present invention were sprinkled on each leaf for 20 seconds by means of a spray gun.

After sprinkling, the resultant leaves were allowed to stand for 48 hours in a green house.

The death and life of the mites were observed by means of a binocular stereomicroscope to calc-late an acaricidal rate. Thereafter, the dead and living mites were removed from each of the leaves and the number of eggs was counted. The leaves were left in the green house for 7 days and the number of unhatched eggs was examined by means of a binocular stereomicroscope to obtain an egg-killing rate. The results are shown in Table (III).

The leaves were not demaged by the compounds of the present invention.

TABLE (III)

| Compound No. | Morality Rate of Citrus Red Mite Mortality Rate | |
|---|---|---|
| | Imago % | Egg % |
| 5 | 95 | 100 |
| 6 | 100 | 100 |
| 7 | 76 | 78 |
| 11 | 100 | 100 |
| 12 | 100 | 100 |
| 13 | 75 | 74 |
| 19 | 85 | 88 |
| 20 | 100 | 100 |
| 21 | 70 | 74 |

TABLE (III)-continued

| Compound No. | Morality Rate of Citrus Red Mite Mortality Rate | |
|---|---|---|
| | Imago % | Egg % |
| 22 | 85 | 86 |
| 23 | 100 | 100 |
| 24 | 75 | 72 |
| Non-treated | 19 | 13 |

We claim:
1. A compound represented by the formula:

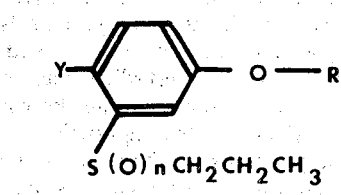

wherein Y represents methyl radical or chlorine atom, R represents an alkyl having from 2 to 7 carbon atoms, $n$ is an integer of 0 and 1.

* * * * *